(12) United States Patent
Hodson et al.

(10) Patent No.: US 7,367,333 B2
(45) Date of Patent: May 6, 2008

(54) INHALATION DEVICE

(75) Inventors: Darren Hodson, Shropshire (GB);
Jorgen Rasmussen, Struer (DK)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/698,950

(22) Filed: Nov. 3, 2003

(65) Prior Publication Data

US 2004/0139967 A1 Jul. 22, 2004

Related U.S. Application Data

(63) Continuation of application No. 09/986,941, filed on Nov. 13, 2001, now abandoned, which is a continuation of application No. 09/214,757, filed as application No. PCT/SE98/02038 on Nov. 11, 1998, now abandoned.

(30) Foreign Application Priority Data

Nov. 14, 1997 (SE) .................................... 9704185

(51) Int. Cl.
*A61M 15/00* (2006.01)
*A61M 11/00* (2006.01)
(52) U.S. Cl. ..................... 128/200.23; 128/200.14; 604/275; 239/337
(58) Field of Classification Search ................................ 128/200.14–200.24
See application file for complete search history.

(56) References Cited

U.S. PATENT DOCUMENTS

| 3,521,643 | A | * | 7/1970 | Toth ...................... 128/202.21 |
| 3,739,950 | A | | 6/1973 | Gorman |
| 4,641,644 | A | | 2/1987 | Andersson et al. |
| 5,334,019 | A | * | 8/1994 | Goldsmith et al. ........... 433/88 |
| 5,520,166 | A | * | 5/1996 | Ritson et al. .......... 128/200.14 |
| 6,267,749 | B1 | | 7/2001 | Miklos et al. |
| 6,427,684 | B2 | | 8/2002 | Ritsche et al. |
| 6,494,201 | B1 | | 12/2002 | Welik |

FOREIGN PATENT DOCUMENTS

| WO | 95/07723 | 3/1995 |
| WO | 96/04949 | 2/1996 |
| WO | WO 96/04948 | 2/1996 |

* cited by examiner

*Primary Examiner*—Glenn K. Dawson
(74) *Attorney, Agent, or Firm*—Nixon & Vanderhye

(57) ABSTRACT

Actuator for an inhaler for delivering medicament by inhalation. The actuator includes a main body having a tubular member for receiving a canister containing medicament and having a valve stem extending therefrom, and an outlet assembly, as a part formed separately of the main body, having a mouthpiece for guiding medicament to the mouth of a user and a nozzle block for receiving the valve stem of the canister and delivering medicament from the canister into the mouthpiece. At least a part of the outlet assembly is configured so as to deform and optionally break on withdrawal of the outlet assembly from the main body so as to prevent re-use of the outlet assembly.

26 Claims, 5 Drawing Sheets

INHALATION DEVICE

This application is a continuation of application Ser. No. 09/986,941, filed Nov. 13, 2001, now abandoned which is a continuation of 09/214,757, filed Jan. 12, 1999, now abandoned which is a National Phase under 35 U.S.C. § 371 of PCT/SE98/02038, filed Nov. 11, 1998, the entire content of which is hereby incorporated by reference in this application.

The present invention relates to an actuator for an inhaler for administering medicament by inhalation and to an inhaler including the same.

BACKGROUND OF THE INVENTION

For some time, actuators have been known for delivering metered doses of medicament from aerosol canisters. These actuators comprise a single integral moulding and are usually coloured to identify the medicament being delivered. After use with only one canister the actuator is discarded. This is desirable, since some medicaments which are delivered, will, over time, become deposited in the nozzle block and the mouthpiece of the actuator.

SUMMARY OF THE INVENTION

It is an aim of the present invention to provide an actuator of two-part construction, with the parts being composed of materials having different constitution and configured so as not to be separable without being deformed or broken. Such two-part construction prevents re-use of the actuator, thereby ensuring that the actuator has to be thrown away after use with a single canister, and further allows for the manufacture of a range of actuators by providing the first part as a common part to the range and forming the second part from a material having different constitution and optionally any shape. Typically, the second part can be coloured or have a particular surface finish or decoration according to the medicament to be delivered. In addition, the second part can be formed to have a particular shape, such as that of an animal which may appeal to young children. Such two-part construction is also advantageous for preparing regulatory documentation which will include common data relating to the first part.

U.S. Pat. No. 5,520,166 discloses a cassette for use in an aerosol delivery device. The cassette comprises, as separate parts, a mouthpiece and a housing to one end of which the mouthpiece is attached, but, in being intended to be located within another device, there is no requirement and no suggestion is made of forming the parts of the cassette of materials having different constitution.

Accordingly, the present invention provides an actuator for an inhaler for delivering medicament by inhalation, comprising: a main body comprising a tubular member for receiving a canister containing medicament and having a valve stem extending therefrom; and an outlet assembly, as a part formed separately of the main body, comprising a mouthpiece for guiding medicament to the mouth of a user and a nozzle block for receiving the valve stem of the canister and delivering medicament from the canister into the mouthpiece; wherein at least a part of at least one of the main body and the outlet assembly is configured so as to deform or break on separating the outlet assembly from the main body so as to prevent re-use of the actuator; characterized in that the main body and the outlet assembly are composed of materials having different constitution.

Preferably, the tubular member includes a lateral opening at one end thereof for receiving the outlet assembly at an angle transverse to the length thereof.

Preferably, the tubular member includes an opening at one end thereof through which a canister is in use fitted.

Preferably, the main body further comprises a foot at one end of the tubular member thereof which is configured such that, with a canister fitted therein, the actuator will stand unsupported with the tubular member extending generally vertically.

In one embodiment the bottom surface of the foot includes a recess for receiving a thumb or a finger of a user. Preferably, the recess is concave.

In another embodiment the bottom surface of the foot is flat.

Preferably, the actuator further comprises a breath actuation mechanism.

Preferably, the actuator further comprises a compliance monitor, in particular a dose counter.

In a preferred embodiment the main body comprises one or both of the breath actuation mechanism and the compliance monitor.

In a particularly preferred embodiment the foot comprises one or both of the breath actuation mechanism and the compliance monitor.

Preferably, the outlet assembly is formed as a single integral moulding.

Preferably, the nozzle block includes a bore having an opening for receiving the valve stem of a canister and a spray orifice configured to direct a spray into the mouthpiece.

Preferably, the outlet assembly is configured to deform or be broken in being separated from the main body.

In a preferred embodiment a connection between the mouthpiece and the nozzle block is configured at least in part to break on separating the outlet assembly form the main body.

In a particularly preferred embodiment the connection between the mouthpiece and the nozzle block comprises at least one member connecting a lower part of the mouthpiece with a lower part of the nozzle block and at least one member connecting an upper part of the mouthpiece with an upper part of the nozzle block, with the at least one member connecting a lower part of the mouthpiece with a lower part of the nozzle block being configured to break on separating the outlet assembly from the main body.

Preferably, the main body and the outlet assembly are configured so as to snap-fit together.

In one embodiment the main body and the outlet assembly are composed of entirely different materials.

In another embodiment the main body and the outlet assembly are composed of the same basic material but include different additives such as colour pigment.

In a particularly preferred embodiment the main body and the outlet assembly are of different colour.

The present invention also extends to an inhaler comprising the above-described actuator and a canister containing medicament.

Preferably, the inhaler is a pressurised metered dose inhaler.

BRIEF DESCRIPTION OF THE DRAWINGS

A preferred embodiment of the present invention will now be described hereinbelow by way of example only with reference to the accompanying drawings, in which.

DETAILED DESCRIPTION OF PREFERRED EMBODIMENTS

Figure 1:
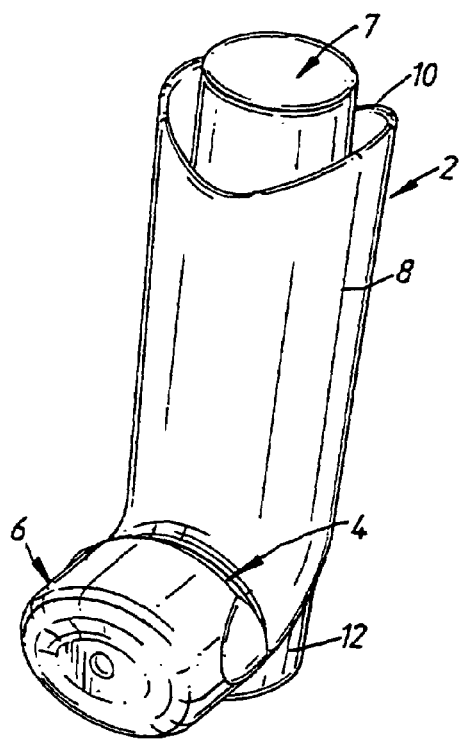
FIG. 1 illustrates a perspective view of an inhaler in accordance with a preferred embodiment of the present invention.
Figure 2:
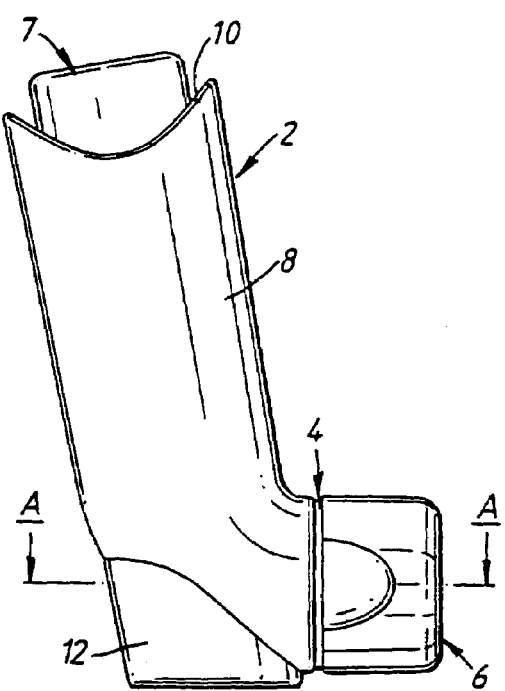
FIG. 2 illustrates a side view of the inhaler of FIG. 1.
Figure 3:
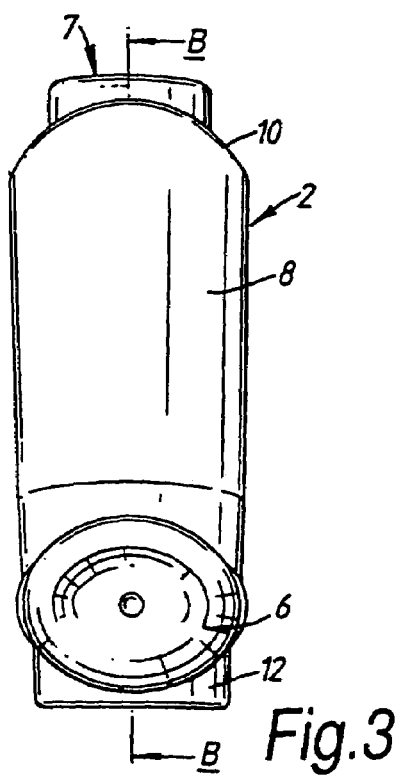
FIG. 3 illustrates a front view of the inhaler of FIG. 1.
Figure 4:
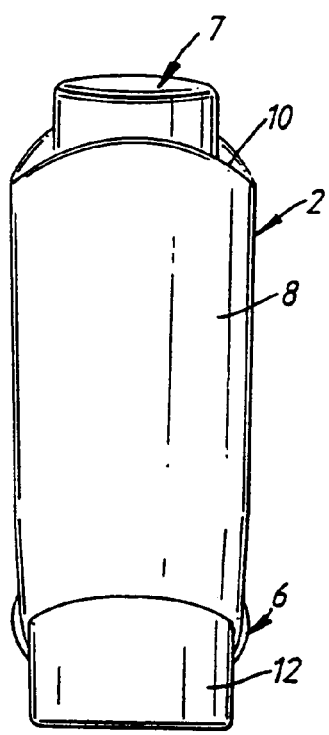
FIG. 4 illustrates a rear view of the inhaler of FIG. 1.
Figure 5:
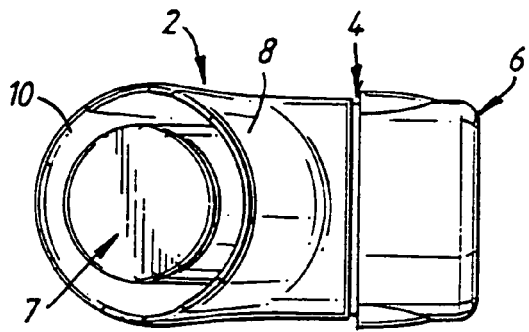
FIG. 5 illustrates a plan view of the inhaler of FIG. 1.
Figure 6:
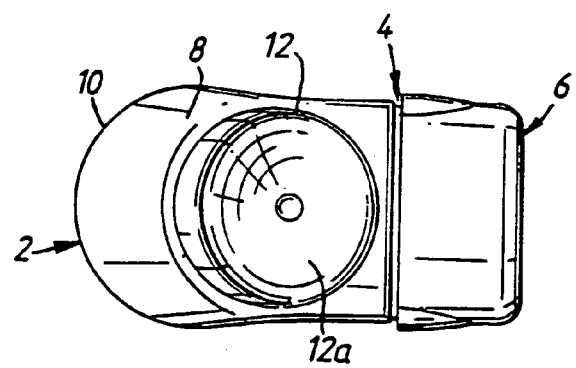
FIG. 6 illustrates an underneath plan view of the inhaler of FIG. 1.
Figure 7:
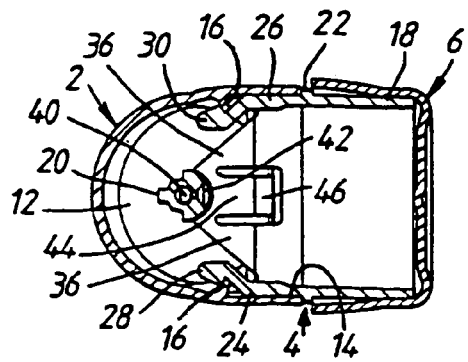
FIG. 7 illustrates a horizontal sectional view (along section A-A) of the inhaler of FIG. 1.
Figure 8:
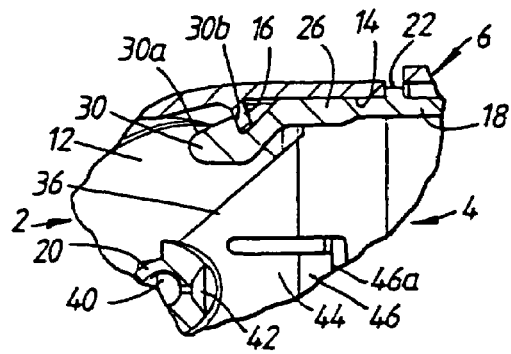
FIG. 8 illustrates in enlarged scale a fragmentary view of the section illustrated in FIG. 7.
Figure 9:
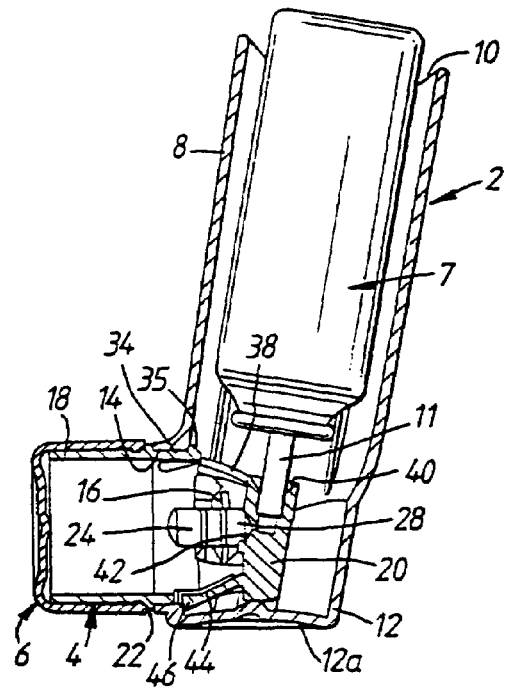
FIG. 9 illustrates a vertical sectional view (along section B-B) of the inhaler of FIG. 1.
Figure 10:
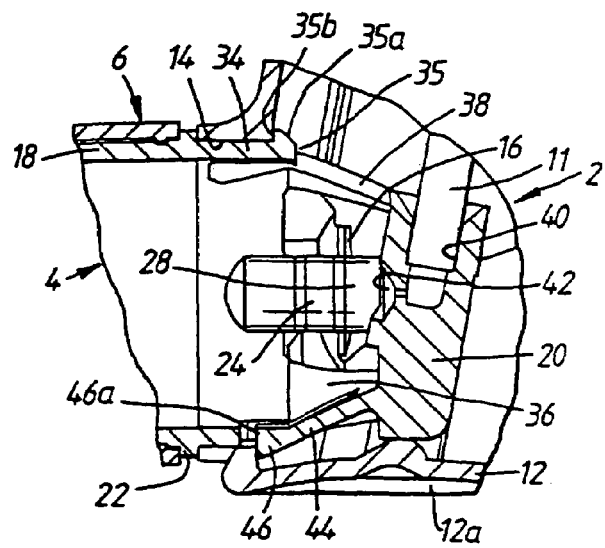
FIG. 10 illustrates in enlarged scale a fragmentary view of the section illustrated in FIG. 9.
Figure 11:
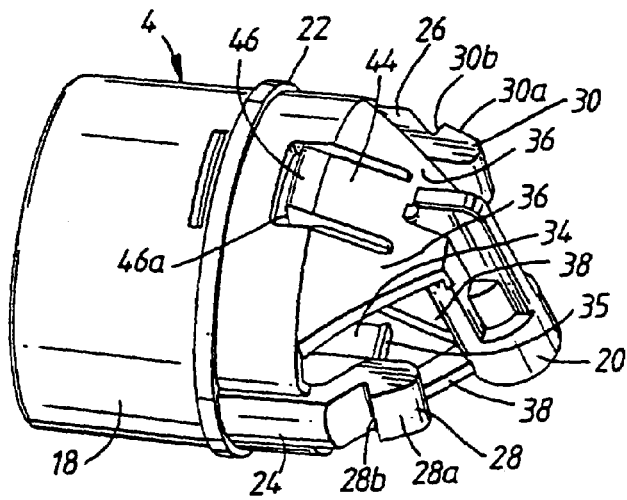
FIG. 11 illustrates a perspective view of the outlet assembly of the actuator of the inhaler of FIG. 1.
Figure 12:
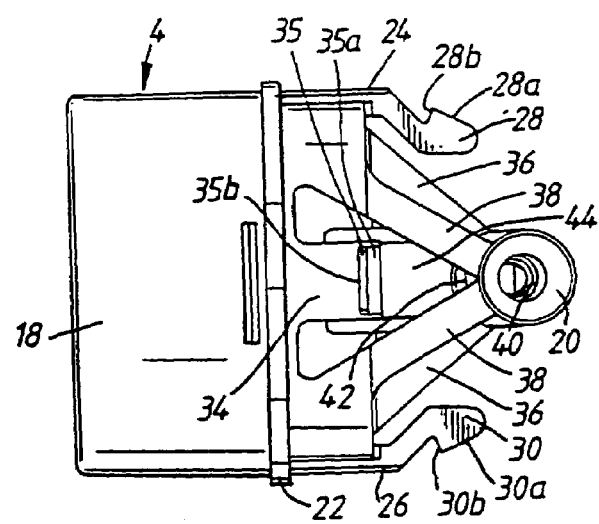
FIG. 12 illustrates a plan view of the outlet assembly of FIG. 11.
Figure 13:
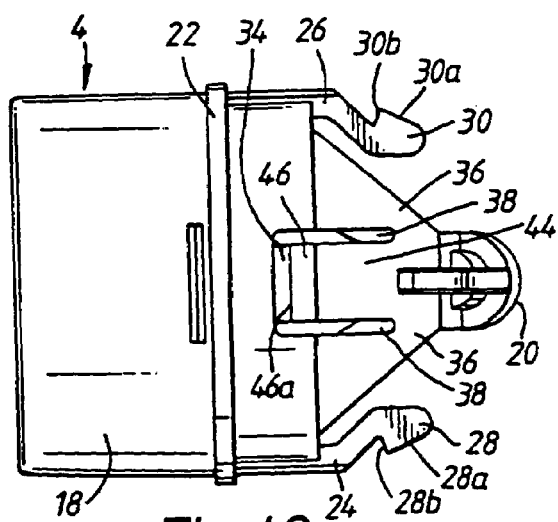
FIG. 13 illustrates an underneath plan view of the outlet assembly of FIG. 11.
Figure 14:
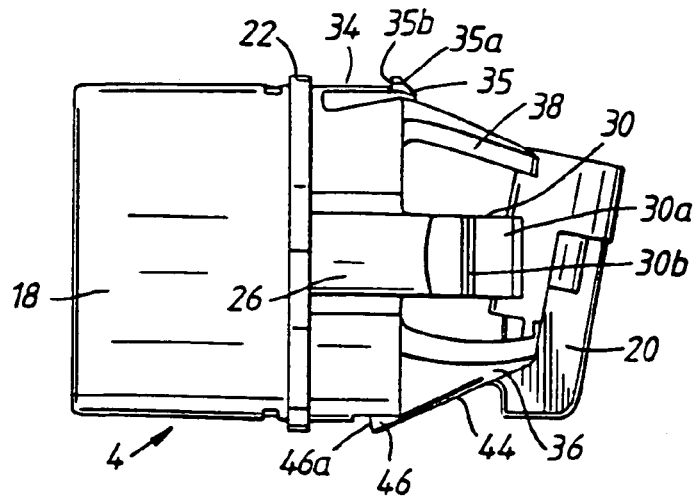
FIG. 14 illustrates a side view of the outlet assembly of FIG. 11.
Figure 15:
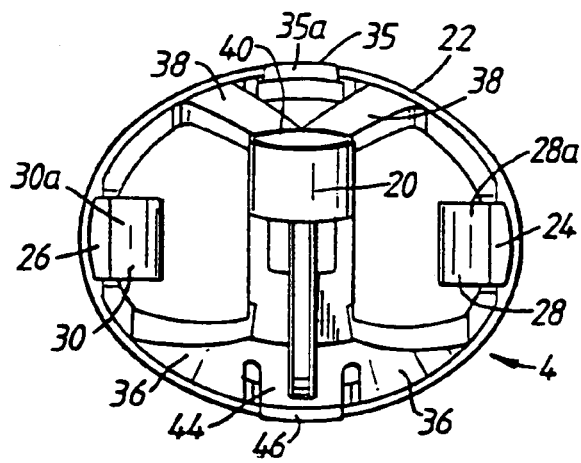
FIG. 15 illustrates a rear view of the outlet assembly of FIG. 11.
Figure 16:
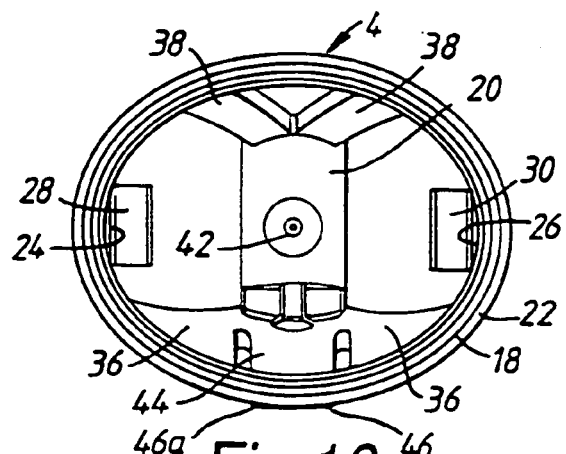
FIG. 16 illustrates a front view of the outlet assembly of FIG. 11.

The inhaler comprises an actuator, which comprises a main body 2, an outlet assembly 4 fitted to a lower part of the main body 2 and a cap 6, and an aerosol canister 7 containing medicament fitted therein.

The main body 2 comprises a tubular member 8 having an opening 10 at one, the upper, end thereof into which a canister 7 having a valve stem 11 extending therefrom is in use fitted, and a foot 12 having a bottom surface which includes a recess 12a, in this embodiment concave in shape, for receiving typically a thumb of a user. In an alternative embodiment the foot 12 can be formed with a substantially flat bottom surface. The foot 12 serves to allow the actuator to stand unsupported on a flat surface such that, when the actuator is not in use, it can be stored in an upright position. This is particularly advantageous when an a canister 7 is fitted therein, since such canisters 7 should, ideally, be stored with the valve stem 11 directed downwards. The other, lower, end of the tubular member 8 is closed and includes a lateral opening 14, in this embodiment ovoid in shape, into which the outlet assembly 4 is fitted.

The main body 2 further comprises a pair of opposing projections 16 which extend inwardly from the inner surface of the tubular member 8 adjacent the lateral opening 14. The projections 16 are disposed to the sides of the lateral opening 14 and are spaced rearwardly therefrom.

The outlet assembly 4 comprises a tubular section 18, a major part of which defines the mouthpiece which is in use gripped by the lips of a user, and a nozzle block 20 connected thereto.

The tubular section 18 includes a radial outwardly-directed peripheral flange 22. When the outlet assembly 4 is inserted fully into the main body 2, the flange 22 abuts the lateral opening 14 such that the major part of the tubular section 18 extends outwardly of the main body 2.

The outlet assembly 4 further comprises first and second arms 24, 26 which extend rearwardly form respective sides of the tubular section 18. Each of the first and second arms 24, 26 includes a catch member 28, 30 which is adapted to engage with a respective one of the projections 16 on the inner surface of the tubular member 8 when the outlet assembly 4 is inserted fully into the main body 2. The catch members 28, 30 on the first and second arms 24, 26 each include a first surface 28a, 30a which has a rearwardly-directed component and acts as a guiding surface, and a second surface 28b, 30b which is substantially orthogonally directed to the longitudinal axis of the outlet assembly 4 and acts as a locking surface.

The outlet assembly 4 further comprises a third arm 34 which extends rearwardly from the top of the tubular section 18. The third arm 34 includes a catch member 35 in the form of an outwardly-directed projection, which, when the outlet assembly 4 is inserted fully into the main body 2, engages behind a part of the tubular member 8 defining the lateral opening 14. The catch member 35 on the third arm 34, as with the catch members 28, 30 on the first and second arms 24, 26, includes a first surface 35a which has a rearwardly-directed component and acts as a guiding surface, and a second surface 35b which is substantially orthogonally directed to the longitudinal axis of the outlet assembly 4 and acts as a locking surface.

The nozzle block 20 is connected to the tubular section 18 by first and second pairs of connecting elements 36, 38. The first pair of connecting elements 36 extend between a lower part of the nozzle block 20 and a lower part of the tubular section 18. As will be described hereinbelow, in this embodiment the lower connecting elements 36 are configured to break or be permanently deformed on withdrawal of the outlet assembly 4 from the main body 2. The second pair of connecting elements 38 extend between an upper part of the nozzle block 20 and an upper part of the tubular section 18. The nozzle block 20 includes a tubular bore 40 which extends along the longitudinal axis of the tubular member 8 when the outlet assembly 4 is inserted fully into the main body 2. The tubular bore 40 is open at one, the upper, end and includes a laterally-directed spray orifice 42 at the other, lower, end. The spray orifice 42 is configured to direct a spray into the tubular section 18. In this embodiment the tubular bore 40 is adapted to receive the valve stem 11 of a canister 7.

The outlet assembly 4 further comprises a fourth arm 44 which extends forwardly and downwardly from the nozzle block 20. The distal end of the fourth arm 44 includes a catch member 46 which, when the outlet assembly 4 is inserted fully into the main body 2, engages behind a part of the tubular member 8 defining the lateral opening 14. The catch member 46 on the fourth arm 44 includes a surface 46a which is substantially orthogonally directed to the longitudinal axis of the outlet assembly 4 and acts as a locking surface.

In manufacture, an outlet assembly 4 and a main body 2 are selected according to the requirements, based on colour, shape, etc., for the actuator. The outlet assembly 4 is then inserted into the lateral opening 14 in the main body 2 until the catch members 28, 30 on the first and second arms 24, 26 of the outlet assembly 4 engage with the respective projections 16 on the inner side surface of the tubular member 8 of the main body 2, and the catch members 34, 46 on the third and fourth arms 34, 44 of the outlet assembly 4 engage behind respective parts of the tubular member 8 defining the lateral opening 14. A canister 7 is then passed into the tubular member 8 of the main body 2 through the upper opening 10 such that the valve stem 11 of the canister 7 is located in the tubular bore 40 in the nozzle block 20. The inhaler is then ready for use.

By the provision of catch members the outlet assembly 4 is held in the main body 2 and the outlet assembly 4 cannot be non-destructably detached from the main body 2. As mentioned hereinabove, the outlet assembly 4 is configured to break or be permanently deformed if withdrawn from the main body 2 and thereby render the outlet assembly 4 and hence the actuator unusable. In this embodiment this is achieved by configuring the lower connecting elements 36 connecting the tubular section 18 and the nozzle block 20 of the outlet assembly 4 to break or be permanently deformed on withdrawal of the outlet assembly 4 from the main body 2.

Finally, it will be understood by a person skilled in the art that the present invention is not limited to the described embodiment but can be modified in many different ways within the scope of the appended claims.

The invention claimed is:

1. An actuator for an inhaler for delivering medicament by inhalation, comprising: a main body comprising a tubular member for receiving a canister containing medicament and having a valve stem extending therefrom; and an outlet assembly, as a part formed separately of the main body, comprising a mouthpiece for guiding medicament to the mouth of a user and a nozzle block for receiving the valve stem of the canister and delivering medicament from the canister into the mouthpiece; wherein the outlet assembly comprises at least one member connecting a lower part of the mouthpiece with a lower part of the nozzle block and at least one member connecting an upper part of the mouthpiece with an upper part of the nozzle block, wherein at least one of said members connecting the mouthpiece with the nozzle block is formed with a weakened section, and wherein the outlet assembly comprises a catch member arranged to apply a deforming force on the weakened section of the connecting member on withdrawal of the outlet assembly from the main body.

2. The actuator according to claim 1, wherein a connection between the mouthpiece and the nozzle block is configured at least in part to deform and optionally break on withdrawal of the outlet assembly from the main body.

3. The actuator according to claim 2, wherein the at least one member connecting a lower part of the mouthpiece with a lower part of the nozzle block being configured to deform and optionally break on withdrawal of the outlet assembly from the main body.

4. The actuator according to claim 1, wherein the tubular member includes a lateral opening at one end thereof for receiving the outlet assembly at an angle transverse to the length thereof.

5. The actuator according to claim 1, wherein the main body being provided with an alignment/support structure for the nozzle block arranged to support the nozzle block in the generally vertical direction during actuation of a canister inserted in the actuator.

6. The actuator according to claim 1, wherein the main body further comprises a foot at one end of the tubular member thereof which is configured such that, with a canister fitted therein, the actuator will stand unsupported with the tubular member extending generally vertically.

7. The actuator according to claim 6, wherein the bottom surface of the foot includes a recess for receiving a thumb or a finger of a user.

8. The actuator according to claim 7, wherein the recess is concave.

9. The actuator according to claim 6, wherein the bottom surface of the foot is flat.

10. The actuator according to claim 6, wherein the foot comprises one or both of a breath actuation mechanism and a compliance monitor.

11. The actuator according to claim 1, further comprising a breath actuation mechanism.

12. The actuator according to claim 11, wherein the main body comprises the breath actuation mechanism.

13. The actuator according to claim 11, wherein the main body comprises one or both of the breath actuation mechanism and a compliance monitor.

14. The actuator according to claim 1, further comprising a compliance monitor.

15. The actuator according to claim 14, wherein the compliance monitor is a dose counter.

16. The actuator according to claim 1, wherein the outlet assembly is formed as a single integral moulding.

17. The actuator according to claim 1, wherein the nozzle block includes a bore having an opening for receiving the valve stem of a canister and a spray orifice configured to direct a spray into the mouthpiece.

18. The actuator according to claim 1, wherein the main body and the outlet assembly are configured so as to snap-fit together.

19. The actuator according to claim 1, wherein the main body and the outlet assembly are of different colour.

20. An inhaler comprising the actuator according to claim 1 and a canister containing medicament.

21. The inhaler according to claim 20, wherein the inhaler is a pressurised metered dose inhaler.

22. An outlet assembly of an actuator for an inhaler for delivering medicament by inhalation, the outlet assembly being a part formed separately of a main body of the actuator, the outlet assembly comprising a nozzle block for receiving a valve stem of a canister containing medicament and delivering medicament from the canister into a mouthpiece for guiding medicament to the mouth of a user, the main body of the actuator comprising a tubular member for receiving the canister, wherein at least a part of the outlet assembly is configured so as to deform and optionally break, to displace the nozzle block out of operable position, on withdrawal of the outlet assembly from the main body, wherein the outlet assembly further comprises at least one member connecting a lower part of the mouthpiece with a lower part of the nozzle block and at least one member connecting an upper part of the mouthpiece with an upper part of the nozzle block, wherein at least one of said members connecting the mouthpiece with the nozzle block is formed with a weakened section, and wherein the outlet assembly comprises a catch member arranged to apply a deforming force on the weakened section of the connecting member upon said withdrawal of the outlet assembly from the main body.

23. The outlet assembly according to claim 22, wherein a connection between the mouthpiece and the nozzle block is configured at least in part to deform and optionally break on withdrawal of the outlet assembly from the main body.

24. The outlet assembly according to claim 23, wherein the at least one member connecting a lower part of the mouthpiece with a lower part of the nozzle block being configured to deform and optionally break on withdrawal of the outlet assembly from the main body.

25. The outlet assembly according to claim 22, wherein it is arranged to be inserted in a lateral opening at one end of, and at an angle transverse to the tubular member.

26. The outlet assembly according to claim 22, wherein it comprises snap fit catch members to enable snap fit connection with a main body.

* * * * *